(12) United States Patent
Ozaki

(10) Patent No.: US 7,749,449 B2
(45) Date of Patent: Jul. 6, 2010

(54) LIQUID DELIVERY APPARATUS AND LIQUID DELIVERY METHOD

(75) Inventor: Nobuhiko Ozaki, Kanagawa (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/347,480

(22) Filed: Dec. 31, 2008

(65) Prior Publication Data
US 2009/0118112 A1 May 7, 2009

Related U.S. Application Data

(63) Continuation of application No. PCT/JP2007/062695, filed on Jun. 25, 2007.

(30) Foreign Application Priority Data

Jul. 11, 2006 (JP) .............................. 2006-190275

(51) Int. Cl.
  *B01L 3/02* (2006.01)
(52) U.S. Cl. .................................................. 422/100
(58) Field of Classification Search .................. 422/100
  See application file for complete search history.

(56) References Cited

U.S. PATENT DOCUMENTS 7,497,996 B2 * 3/2009 Ozaki et al. ................. 422/100

FOREIGN PATENT DOCUMENTS

WO  WO 2006077695 A1 *  7/2006

OTHER PUBLICATIONS

English translation of the International Preliminary Report on Patentability and Written Opinion issued in International Application No. PCT/JP2007/062695, dated Jun. 25, 2007.
Thilo Brenner, et al., "A Flow Switch Based on Coriolis Force", Proceedings of μTAS 2003, Seventh International Conference on Micro Total Analysis Systems, Oct. 2003, vol. 2, pp. 903-906.

* cited by examiner

Primary Examiner—Walter D Griffin
Assistant Examiner—Bobby Ramdhanie
(74) Attorney, Agent, or Firm—McDermott Will & Emery LLP

(57) ABSTRACT

A chamber chip 17 is provided with a pre-branching chamber 21, branching chamber 22, and a guiding fluid passage 24 for these chambers 21. The branching chamber 22 has a separation wall 23 which defines two branching compartments 29A and 29B. A wall surface of the branching chamber positioned at a side of the rotary shaft 13 has a spread angle θe from an outlet end section 24b of the guiding fluid passage 24 which is an obtuse angle. The rotation of the chamber chip 17 about the rotary shaft 13 causes a liquid 23 to flow from the pre-branching chamber 21 through the guiding fluid passage 24 into the branching chamber 22. By a Coriolis force acting in an opposite direction to a rotation direction R1, R2 about the rotary shaft 13, the liquid 23 is selectively supplied to any one of the branching compartments 29A and 29B.

5 Claims, 13 Drawing Sheets

PRIOR ART

LIQUID DELIVERY APPARATUS AND LIQUID DELIVERY METHOD

This is a continuation application of International Application No. PCT/JP2007/062695, filed on Jun. 25, 2007.

BACKGROUND OF THE INVENTION

The present invention relates to a liquid delivery apparatus and a liquid delivery method. More particularly the present invention relates to a liquid delivery apparatus and a liquid delivery method for delivering a small volume of liquid while controlling the flow thereof in a micro fluid passage.

In recent years, various bio-sensors have been developed for use as medical checkup chips in POCT (point of care test) applications at clinics or homes. Many of these bio-sensors are card-type devices having a micro fluid passage structure called μTAS (micro total analysis system). In view of simplification of the device structure, bio-sensors of this type require technologies for quantitatively delivering and distributing small volumes of liquid without use of a mechanical valve.

For example, Thilo Brenner et al., "Flow switch based on Coriolis force"; 6th International Conference of Miniaturized Chemical and Biochemical Analysis Systems (μTAS2003), October 2003; pp. 903-906 discloses a structure that distributes a fluid selectively among two chambers by using a Coriolis force. The Coriolis force is an apparent force (a kind of inertial force) that acts on an object, which moves on a rotating coordinate system, in a direction opposite to the direction of rotation (perpendicular to the direction of motion) with a strength proportional to the rotation speed and the moving speed of the object. Referring to FIG. 14, a rotary platform 1 has a fluid passage 2 connected to a chamber on the supply side (not shown) and fluid passages 4A, 4B that branch from the fluid passage 2 and are respectively connected to post-branching chambers 3A, 3B. The fluid passages 2, 4A, and 4B constitute a branching structure of inverted Y-like shape. The liquid in the supply chamber is caused by centrifugal force to flow through the fluid passage 2 into either the fluid passage 4A or 4B. When the rotary platform 1 rotates clockwise in plan view as indicated by a symbol R1, the fluid receives a Coriolis force acting counterclockwise. This results in that the fluid flows into the fluid passage 4B positioned at the counterclockwise side with respect to the outlet of the fluid passage 2 as indicated by an arrow 5B. Contrarily to this, when the rotary platform 1 rotates counterclockwise in plan view as indicated by a symbol R2, the fluid receives a Coriolis force acting clockwise in plan view. This results in that the fluid flows into the fluid passage 4A positioned at the clockwise with respect to the outlet of the fluid passage 2 as indicated by arrow 5A.

Experiments and simulations described in the above-mentioned prior art document show that under the condition where the fluid passage is 360 μm in width and 125 μm in depth, if the rotation speed of the rotary platform 1 is not lower than about 3,300 rpm, then the fluid can be selectively delivered into either one of the fluid passages 4A and 4B depending on the rotation direction of the rotary platform 1. However, the rotation speed decreased to about 2,000 rpm or lower causes that the fluid flows into the other fluid passage that is not selected and the rotation speed decreased to about 1,000 rpm or lower causes that the amount of incoming fluid becomes equal between the fluid passages 4A and 4B. In other words, the branching structure having the inverted Y-like shape shown in FIG. 14 can not achieve the selective distribution of liquid under the condition where the rotation speed is relatively low.

SUMMARY OF THE INVENTION

In consideration of the problems of the conventional art described above, it is an object of the present invention to provide a liquid delivery apparatus capable of selectively distributing a liquid by using a Coriolis force even when a rotation speed of a rotary platform is low.

According to various experiments and investigations conducted by the present inventors it is supposed that a kind of Coanda effect is the cause for that the branching structure of inverted Y-like shape of the above-mentioned prior art document can not achieve selective distribution of the liquid at the low rotation speed of the rotary platform. Specifically, it is hypothesized that attachment vortices are generated on the outer wall surface of the branching section of inverted Y shape, and a pressure drop due to the attachment vortices cause the liquid to stagnate or stick on the outer wall surface of the branching section. Based on such assumption, the inventor of this application found a structure that enables selective distribution of a liquid by making use of a Coriolis force even when the rotation speed is relatively low.

A first aspect of the present invention provides liquid delivery apparatus comprising: a rotary platform capable of rotating about a center of rotation; a pre-branching chamber provided in the rotary platform and accommodating a liquid; a guiding fluid passage provided in the rotary platform, having an inlet end section that is connected to the pre-branching chamber and holds the liquid in the pre-branching chamber by a capillary force, extending from the inlet end section in a direction away from the center of rotation, and having an outlet end section at an opposite side to the inlet end section; a branching chamber provided in the rotary platform at a position farther from the center of rotation than the pre-branching chamber, spatially enclosed except for an air aperture, and having a first wall surface that is arranged at a centripetal direction side and at which the outlet end section of the guiding fluid passage opens, second wall surface that is arranged at a centrifugal direction side and is opposed to the first wall surface, and separation wall that extends from the second wall surface toward the first wall surface to define a plurality of branching compartments, wherein the first wall surface has a spread angle from the outlet end section of the guiding fluid passage that is an obtuse angle at least in a direction of arrangement of the plurality of branching compartments, and the separation wall has a distal end that is arranged in the vicinity of a imaginary line extending in the centrifugal direction from the outlet end section of the guiding fluid passage and opposed to the first wall surface with a distance; and a rotation drive unit for rotating the rotary platform about the center of rotation at a speed rotation speed between 600 rpm and 2000 rpm, wherein the liquid is a blood serum, and wherein a cross sectional area of the guiding fluid passage is in a range between 1 μm$^2$ and 4 mm$^2$.

preferably, the spread angle of the first wall surface is between 120 degrees and 300 degrees.

The liquid is held in the pre-branching chamber by capillary force acting at the inlet end section of the guiding fluid passage. As the rotation drive unit causes the rotary platform to rotate, a centrifugal force is exerted onto the liquid in the pre-branching chamber held at the inlet end section. When the rotary platform reaches a certain rotation speed at which the centrifugal force exceeds the capillary force, the liquid in the pre-branching chamber flows through the guiding fluid passage into the branching chamber via the outlet end section. A Coriolis force acting in a direction opposite to the rotation direction of the rotary platform acts on the liquid that flows into the branching chamber. A route of the liquid that flows into the branching chamber is deflected by the Coriolis force with respect to the centrifugal direction. The distal end of the separation wall that defines the branching compartments is the vicinity of the imaginary line extending in the centrifugal direction from the outlet end section. Therefore, the inflowing liquid the route thereof deflected by the Coriolis force flows into one of the branching compartments that are separated from each other by the separation wall. Specifically, the liquid in the pre-branching chamber flows through the guiding fluid passage into the branching compartment positioned opposite to the rotation direction of the rotary platform with respect to the separation wall. For example, when the rotary platform rotates clockwise, the liquid flows into the branching compartment positioned in an anticlockwise direction to the separation wall and, when the rotary platform rotates counterclockwise, the liquid flows into the branching compartment positioned in a clockwise direction to the separation wall.

Since the spread angle of the first wall surface from the outlet end section of the guiding fluid passage is the obtuse angle in the direction of arrangement of the compartments, the liquid can be selectively distributed into the branching compartments by the Coriolis force even when the rotation speed of the rotary platform is relatively low. Specifically, the liquid can be selectively distributed into the branching compartments when the rotation speed of the rotary platform is between 600 rpm and 3,300 rpm, particularly between 600 rpm and 2,000 rpm. The reason for this is supposed that influence of the Coanda effect is reduced due to that the spread angle is the obtuse angle. Specifically, it is supposed that occurrence of attachment vortexes on the first wall surface in the vicinity of the outlet end section is suppressed due to the obtuse spread angle, resulting in that the liquid is suppressed from being stagnating or attached to the first wall surface in the vicinity of the outlet due to a pressure drop caused by the attachment of vortices.

The pre-branching chamber may be either a chamber into which the liquid is directly filled or a chamber into which the liquid flows through a fluid passage from another chamber positioned upstream. Further, any or all of the plurality of branching compartments may be connected to the chamber positioned downstream via a fluid passage.

A second aspect of the present invention provides a liquid delivery method. First, a rotary platform is prepared. The rotary platform comprises a pre-branching chamber, a guiding fluid passage having an inlet end section that is connected to the pre-branching chamber and an outlet end section at an opposite side to the inlet end section and having a cross sectional area in a range between 1 $\mu m^2$ and 4 $mm^2$; and a branching chamber provided at a position farther from the center of rotation than the pre-branching chamber, spatially enclosed except for an air aperture, and having a first wall surface that is arranged at a centripetal direction side and at which the outlet end section of the guiding fluid passage opens, second wall surface that is arranged at a centrifugal direction side and is opposed to the first wall surface, and separation wall that extends from the second wall surface toward the first wall surface to define a plurality of branching compartments, wherein the first wall surface has a spread angle from the outlet end section of the guiding fluid passage that is an obtuse angle at least in a direction of arrangement of the plurality of branching compartments, and the separation wall has a distal end that is arranged in the vicinity of a imaginary line extending in the centrifugal direction from the outlet end section of the guiding fluid passage and is opposed to the first wall surface with a distance. Then, a blood serum is supplied to the pre-branching chamber so that the blood serum is held in the pre-branching chamber by a capillary force at the inlet end section of the guiding fluid passage. After that, the rotary platform is rotated about the center of rotation at a rotation speed between 600 rpm and 2000 rpm so that a centrifugal force exceeding the capillary force is exerted on the blood serum, thereby causing the blood serum in the pre-branching chamber to flow through the guiding fluid passage into the branching compartment positioned opposite to a rotation direction of the rotary platform with respect to the separation wall.

According to the liquid delivery apparatus and the liquid delivery method of the present invention, because spread angle of the first wall surface from the outlet end section of the guiding fluid passage is the obtuse angle in the direction of arrangement of the branching compartments, the liquid can be selectively distributed among the branching compartments by the Coriolis force even when the rotation speed of the rotary platform is relatively low (between 600 rpm and 3300 rpm, particularly between 600 rpm and 2,000 rpm). Further, the rotary platform has a simple structure and an areas required to provide the fluid passages and the chambers in the rotary platform can be decreased. Furthermore, a higher degree of freedom is obtained in designing the structure such as layout of chambers and the fluid passages and volumes of the branching compartments.

BRIEF DESCRIPTION OF THE DRAWINGS

Other objections and characteristics of the present invention shall be clarified by the following description of the preferred embodiments with reference to the accompanying drawings in which.

DETAILED DESCRIPTION OF THE PREFERRED EMBODIMENTS

First Embodiment

Figure 1:
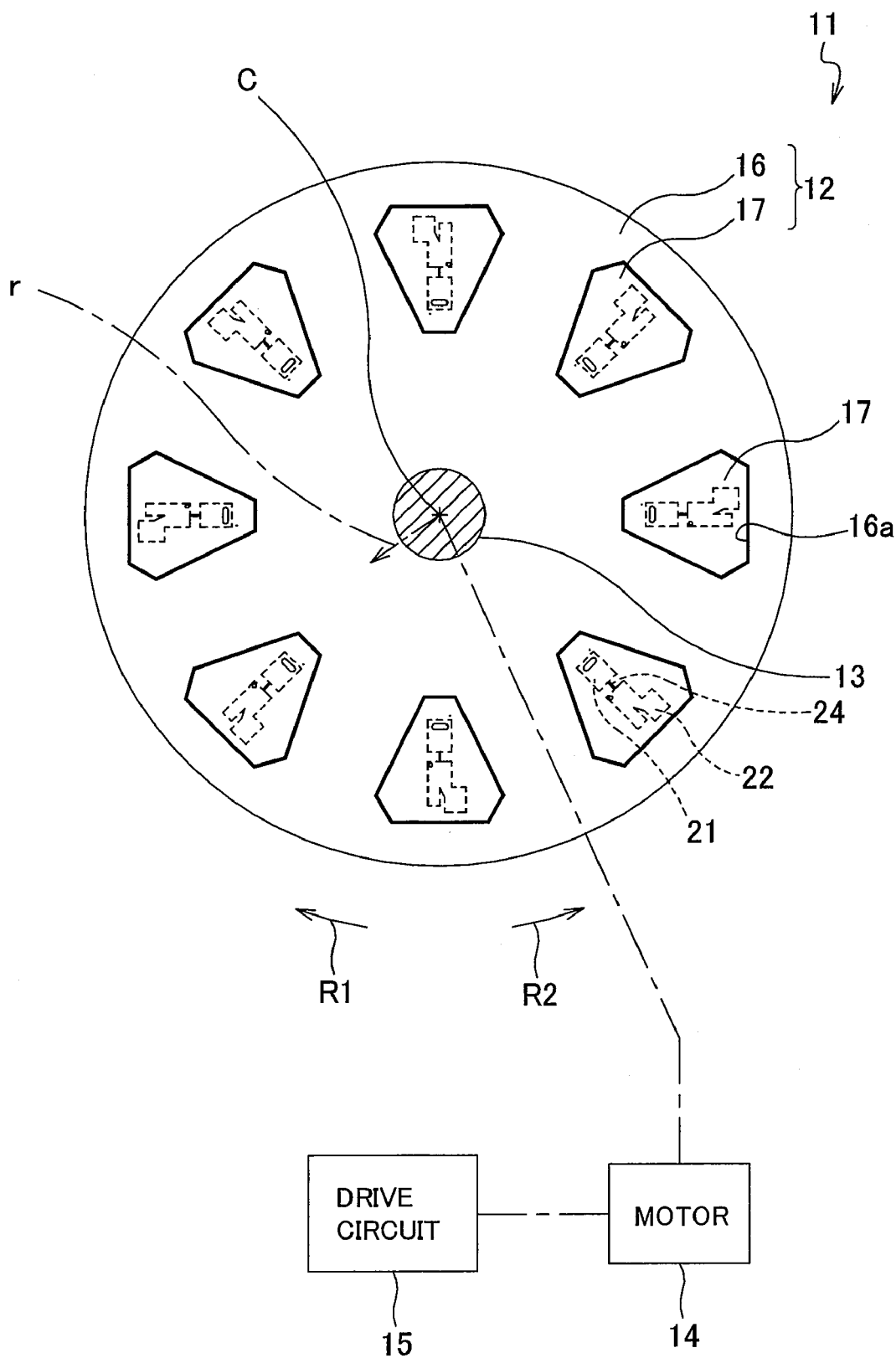
FIG. 1 is a schematic plan view of a liquid delivery apparatus according to a first embodiment of the present invention.
Figure 2:
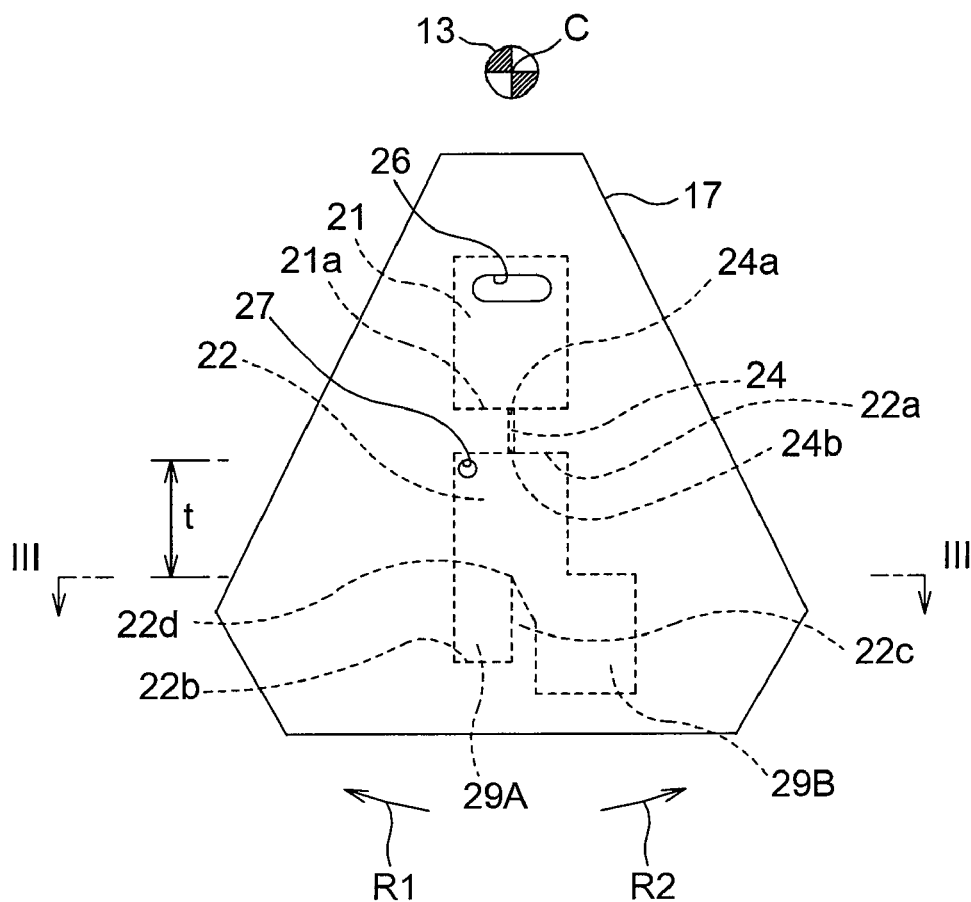
FIG. 2 is a plan view of a chamber chip according to the first embodiment.
Figure 3:
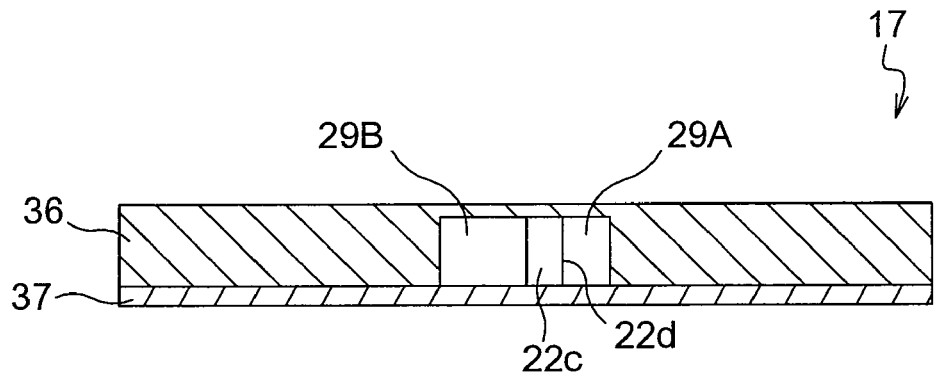
FIG. 3 is a sectional view taken along a line III-III of FIG. 2.

FIGS. 1 to 3 show a liquid delivery apparatus 11 according to a first embodiment of the present invention.

The liquid delivery apparatus 11 comprises a rotary platform 12, a rotary shaft 13 to which the rotary platform 12 is fixed, a motor 14 that rotately drives the rotary shaft 13, and a drive circuit 15 for the motor 14. The rotary shaft 13 is disposed such that the centerline C thereof extends vertically. The rotary platform 12 can be driven to rotate both clockwise R1 and counterclockwise R2 in plan view by the motor 14. In this embodiment, the rotary platform 12 is constituted from a rotary platform body 16 and a plurality of chamber chips 17 that are detachably accommodated in accommodation holes 16a formed in the rotary platform body 16.

The chamber chips 17 will be described with reference to FIGS. 2 and 3. In the following description, positions and orientations with respect to the center of rotation C are defined based on the state in which the chamber chips 17 are mounted on the rotary platform body 16. A pre-branching chamber 21 and branching chamber 22 are formed in each of the chamber chips 17. The branching chamber 22 is positioned farther from the center of rotation C than the pre-branching chamber 21 in plan view. In other words, the branching chamber 22 is positioned farther from the rotary shaft 13 in the radial direction r (refer to FIG. 1) than the pre-branching chamber 21. Further, a guiding fluid passage 24 that extends in the radial direction r of the rotary shaft is formed in the chamber chip 17. The pre-branching chamber 21 and the branching chamber 22 are fluidly connected with each other by the guiding fluid passage 24. As will be described in detail later, a liquid 23 (refer to, for example, FIG. 4) in the pre-branching chamber 21 is caused to flow through the guiding fluid passage 24 selectively into one of two branching compartments 29A and 29B of the branching chamber 22. The liquid 23 is driven to move by a centrifugal force generated by the rotation of the rotary platform 12 and a Coriolis force.

The pre-branching chamber 21 is formed in the chamber chip 17 to be spatially closed. In this embodiment, the pre-branching chamber 21 is a generally rectangular parallelepiped space and is thus rectangular in plan view. The chamber chip 17 has an injection port 26 formed therein so as to penetrate from a top wall of the pre-branching chamber 21 to a top surface of the chamber chip 17, thereby communicating the inside of the pre-branching chamber 21 with the outside of the chamber chip 17. An inlet end section 24a of the guiding fluid passage 24 opens at a wall surface arranged at a centrifugal side of the pre-branching chamber 21, namely the wall surface 21a at an outward position in the radial direction r of the pre-branching surface 21. The injection port 26 is formed at a position nearer to the center of rotation C than the inlet end section 24a of the guiding fluid passage 24.

The branching chamber 22 is a closed space formed in the chamber chip 17, surrounded by a plurality of wall surfaces. In this embodiment, the branching chamber 22 has such a configuration as a long rectangle extending in the radial direc-tion r of the rotary shaft 13 and another rectangle and another rectangle lapped on an outward corner (lower right corner in FIG. 2) of the former rectangle are combined. An outlet end section 24b of the guiding fluid passage 24 opens at a wall surface arranged at a centripetal side of the branching chamber 22, namely the wall surface (first wall surface) 22a at an inward position in the radial direction r of the branching chamber 22 position.

The chamber chip 17 has an air aperture 27 formed therein so as to penetrate from a top wall of the branching chamber 22 through the top surface of the chamber chip 17, thereby fluidly communicating the inside of the branching chamber 22 with the outside of the chamber chip 17. The air aperture 27 has a function of purging the air from the branching chamber 22 to the outside of the chamber chip 17 when the fluid 23 flows into the branching chamber 22.

A separation wall 22c protrudes from a wall surface 22b arranged at the centrifugal side so as to be opposite to the wall surface 22a, namely the wall surface (second wall surface) 22b positioned at an outward position in the radial direction r, toward the wall surface 22a. The separation wall 22c has a proximal integrally connected with the wall surface 22b and a distal end 22d opposed to the wall surface 22a with a distance t. A top end of the separation wall 22c is integral with the top wall of the branching chamber 22 (bottom surface of a upper substrate 36 to be described later) and a bottom end of the separation wall 22c is tightly contact with the bottom wall of the branching chamber 22 (top surface of a lower substrate 37 to be described later). The separation wall 22c divides the inside of the branching chamber 22 into two branching compartments 29A and 29B adjacent to each other. The branching compartments 29A and 29B are arranged side by side in the rotation direction of the rotary platform 12, namely in the direction perpendicular to the radial direction r (right-to-left direction in FIG. 2). In this embodiment, the proximal end of the separation wall 22c has a rectangular shape having a substantially constant width (dimension in a direction perpendicular to the radial direction r) in plan view, whereas the distal end 22d has a tapered shape with an inclined surface on the branching compartments 29B side, i.e., on the right side in FIG. 2. However, the shape of the separation wall 22c is not limited on the condition that the branching compartment 22 can be divided into two branching compartments 29A and 29B in such a state as the distance t with the wall surface 21a can be maintained.

Figure 5:
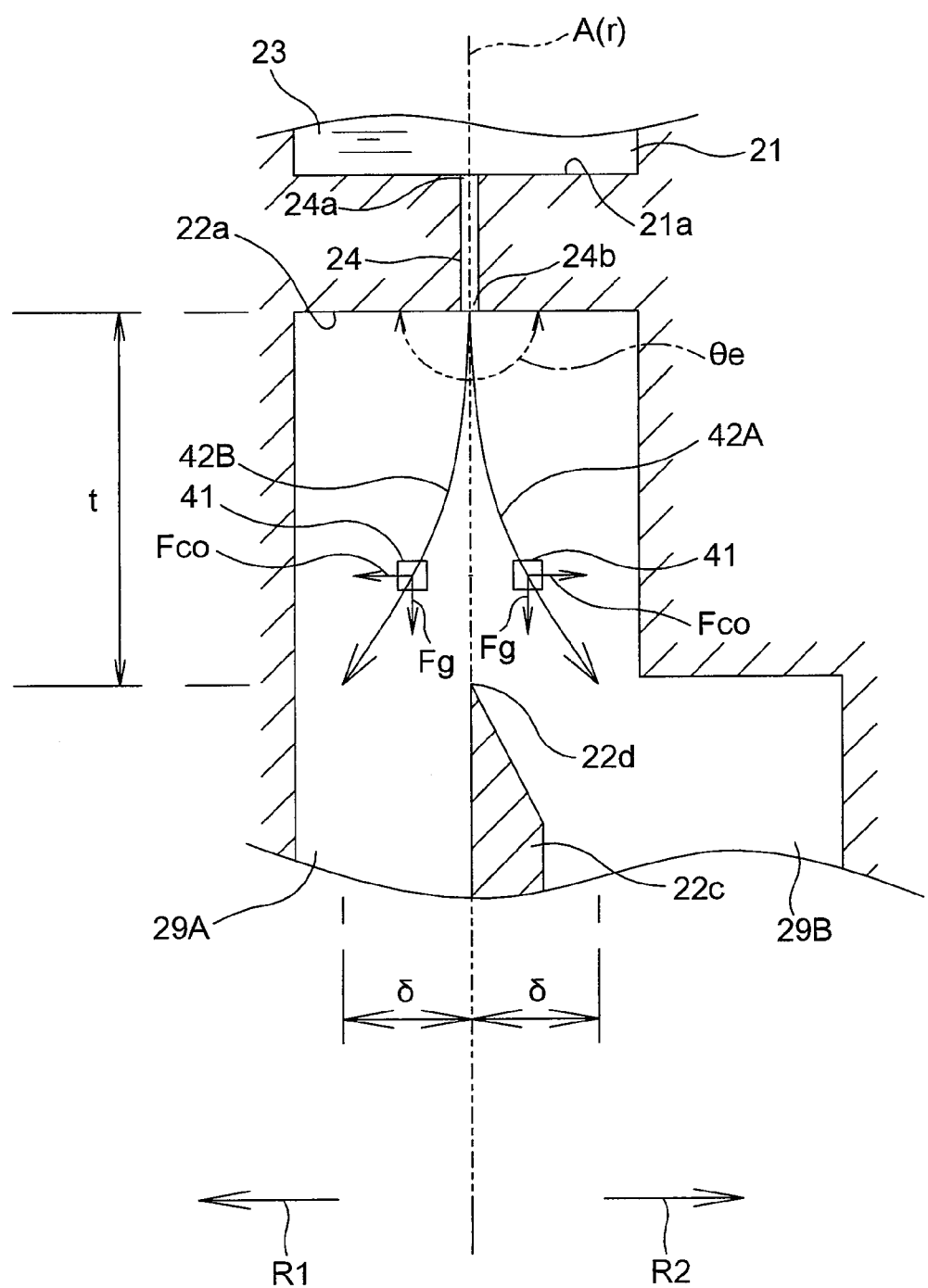
FIG. 5 is a schematic diagram illustrating a Coriolis force and centrifugal force acting on the liquid.

Now reference will be made to FIG. 5 as well as to FIGS. 2 and 3. As described previously, the outlet end section 24b of the guiding fluid passage 24 opens at the wall surface 22a on the inside of the branching chamber 22. In the portion where the outlet end section 24 opens at the wall surface 22a, the space where the liquid 23 passes has such a structure that sharply expands. Specifically, a spread angle θe of the wall surface 22a from the outlet end section 24b of the guiding fluid passage 24 in a direction of arrangement of the branching chambers 29A and 29B, namely in the rotary direction of the rotary platform 12 of in a direction perpendicular to the radial direction r (right-to-left direction in FIG. 2), is set to 180°. Further, a width of the branching chamber 22 on the inner wall surface 22a is set significantly larger than the width of the guiding fluid passage 24 (for example, the former is about 500 to 4,000 μm, whereas the latter is about 50 to 200 μm). As described above, the sharply-expanding structure of the section where the outlet end section 24a of the guiding fluid passage 24 opens at the branching chamber 22 enables selective distribution of the liquid 23 into one of the branching compartments 29A and 29B by the Coriolis force even when the rotation speed of the rotary platform 12 is relatively low.

The spread angle θe of the obtuse angle (for example, in a range between 120 degrees and 300 degrees) can achieve the selective distribution of liquid in such a low rotation speed range and thus the spread angle θe can be arbitrarily set within the range according to conditions such as contact angles of the liquid 23 to the wall surfaces of the fluid passages and chambers.

In this embodiment, the distal end 22d of the separation wall 22c is positioned on an imaginary line A extending in the centrifugal direction from the outlet end section 24b of the guiding fluid passage 24. However, the distal end 22d of the separation wall 22c may be positioned in the vicinity of the imaginary line A. The position of the distal end 22d of the separation wall 22c relative to the imaginary line A can be set arbitrarily according to the amount of shift δ of the liquid 23 at the distal end 22d to be described later on the condition that the liquid 23 can be selectively delivered into one of the branching compartments 29A and 29B by the Coriolis force.

To ensure reliable delivery of the liquid 23 from the pre-branching chamber 21 through the guiding fluid passage 24 into the branching chamber 22, the guiding fluid passage 24 needs to be a fine fluid passage. Specifically, a volume of the guiding fluid passage 24 is preferably equivalent to or less than the volume of the pre-branching chamber 21 and the branching chamber 22. Further, it is preferable that a width and a depth of the guiding fluid passage 24 are smaller than those of the pre-branching chamber 21 and the branching chamber 22. Specifically, a cross sectional area of the guiding fluid passage 24 is in a range between 1 $\mu m^2$ and 4 $mm^2$, preferably between 25 $\mu m^2$ and 100,000 $\mu m^2$, and more preferably 10,000 $\mu m^2$.

Figure 4:
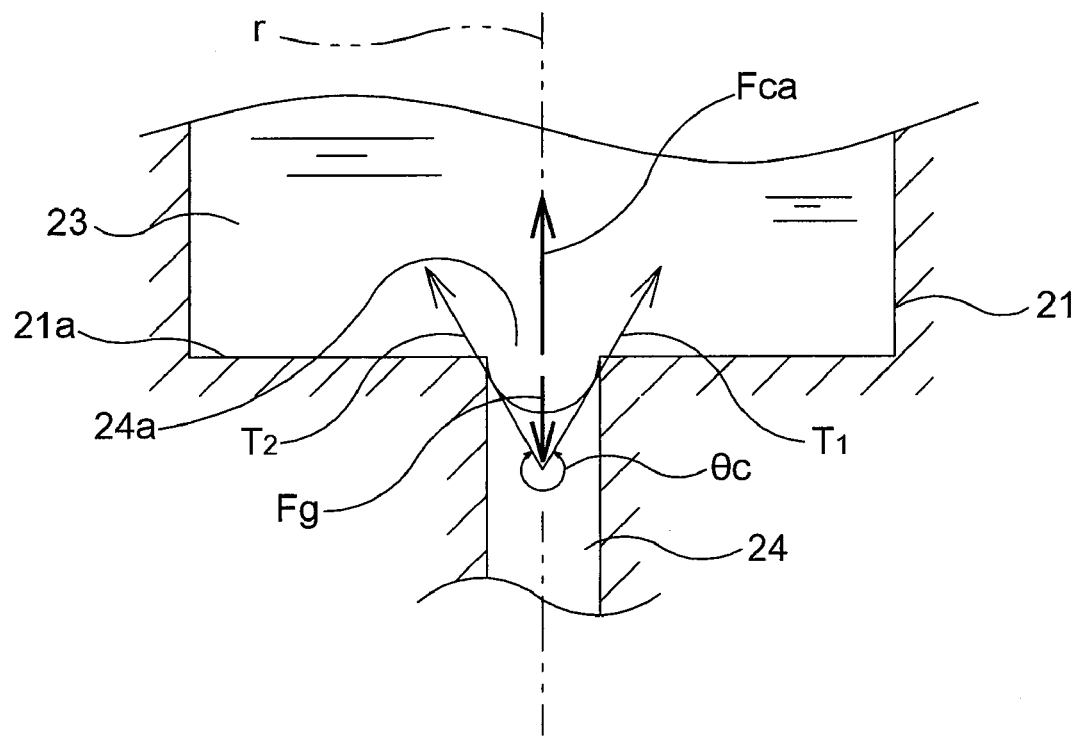
FIG. 4 is a schematic diagram illustrating a capillary force and centrifugal force acting on the liquid.

The inlet end section 24a of the guiding fluid passage 24 fluidly connected to the pre-branching chamber 21 functions as a valve that releasably holds the liquid stored in the pre-branching chamber 21. The valve function will be described in detail. Initially, the inlet end section 24a has hydrophobicity. With reference to FIG. 4, since the guiding fluid passage 24 is made as the fine fluid passage having hydrophobicity, the liquid 23 is held at the inlet end section 24a by the capillary force Fca caused by a surface tension and thus the inside of the guiding fluid passage 24 is not wetted with the liquid 23. The fluid passage surface at the inlet end section 24a having hydrophobicity will not be wetted with the liquid 23 and thus the contact angle θc of the liquid 23 to the fluid passage surface becomes an obtuse angle. Therefore, the capillary force Fca is generated to act so as to hold the liquid 23 within the pre-branching chamber 21. Specifically, surface tensions T1 through Tn are generated in the interface between the fluid passage surface and the liquid and the capillary force Fca that is the resultant force of the surface tensions is directed inward along the radial direction r of the rotary shaft 13. In other words, the capillary force Fca is generated so as to be directed from the inlet end section 24a toward the inside of the pre-branching chamber 21. The magnitude of the capillary force Fca is given by the following equation (1):

$$Fca = T \times \cos\theta c \times c \quad (1)$$

where T represents the surface tension of water, θc represents the contact angle of liquid 9 to the fluid passage surface, and c represents the circumferential length of the fluid passage.

While the wall surface of the inlet end section 24a of the guiding fluid passage 24 has hydrophobicity, the wall surface of the rest of the guiding fluid passage 24 including the outlet end section 24b and the wall surfaces of the pre-branching chamber 21 and the branching chamber 22 may be either hydrophilic or hydrophobic.

With reference to FIG. 3, the chamber chip 17 of this embodiment has a two-layer structure comprising an upper substrate 36 and a lower substrate 37 stacked and bonded together. Formed on the under surface of the upper substrate 36 in the form of recesses having bottoms are the pre-branching chamber 21, the branching chamber 22, and the guiding fluid passage 24. Further, the injection port 26 and the air aperture 27 are formed to penetrate through the upper substrate 36 in the direction of thickness. The lower substrate 37 having no hole or the like formed therein is bonded onto the under surface of the upper substrate 36 is. The laminated structure of the chamber chip 17 is not limited to that of this embodiment and such a structure as three or more substrates are stacked and bonded together may also be employed.

A liquid delivery method using the liquid delivery apparatus 11 of the first embodiment will be described. First, the liquid 23 is poured through the injection port 26 into the pre-branching chamber 21 to be stored the liquid 23 in the pre-branching chamber 21. The liquid 23 is held at the inlet end section 24a so as not to enter the guiding fluid passage 24 by the capillary force Fca generated at the inlet end section 24a of the guiding fluid passage 24 having hydrophobicity (refer to FIG. 4).

Then the rotary platform body 16 is driven to rotate about the rotary shaft 13. A centrifugal force Fg (refer to FIG. 4) caused by the rotation is exerted on the liquid 23 held at the inlet end section 24a of the guiding fluid passage 24 by the capillary force. When the rotation speed of the rotary platform body 16 reaches a certain speed (rotation speed RV1) at which the centrifugal force Fg exceeds the capillary force Fca (equation (1)) acting at the inlet end section 24a of the guiding fluid passage 24, the effect of holding of the liquid 23 at the inlet end section 24a of the guiding fluid passage 24 is lost. As a result, the liquid 23 in the pre-branching chamber 21 flows through the guiding fluid passage 24 and the outlet end section 24b into the branching chamber 22.

The liquid 23 that has entered the branching chamber 22 is subjected to the Coriolis force acting in the direction determined by the rotation direction of the rotary platform 12, resulting in that the liquid 23 selectively flow into either the branching compartment 29A or 29B. Now this effect will be described in detail. With reference to FIG. 5, consideration is given to an infinitesimal element 41 of the liquid 23 having entered through the outlet end section 24b into the branching chamber 22. The centrifugal force Fg acting on the infinitesimal element 41 is given by the following equation (2):

$$Fg = m \times r' \times \omega^2 \quad (2)$$

where m represents the mass of the infinitesimal element 41, r' represents the distance of the infinitesimal element 41 from the center of rotation C, and ω represents the rotation speed (angular speed) of the rotary platform 12.

The centrifugal force F acts toward the outside in the radial direction r. Thus, given that only the centrifugal force F predominantly acts on the infinitesimal element 41 in the moving direction, the infinitesimal element 41 moves toward the outside in the radial direction r regardless of the rotation direction of the rotary platform 12. This means that the liquid 23 flows from the outlet end section 23 toward the outside in the radial direction r regardless of the rotation direction of the rotary platform 12 so as to hit the distal end 22d of the separation wall 22c, thereby delivering the liquid 23 to both of the branching compartments 29A and 29B.

In actuality, however, not only the centrifugal force Fg but also the Coriolis force Fco effects on the moving direction of the infinitesimal element 41. The Coriolis force Fco acting on the infinitesimal element 41 is given by the following equation (3):

$$Fco = 2 \times m \times \omega \times v \qquad (3)$$

where m represents the mass of the infinitesimal element 41, ω represents the rotation speed of the rotary platform 12 (angular velocity), and v represents the velocity of the infinitesimal element 41 moving relative to the rotary platform 12 (chamber chip 17) (the velocity toward the outside in the radial direction r in this example).

Figure 6A:
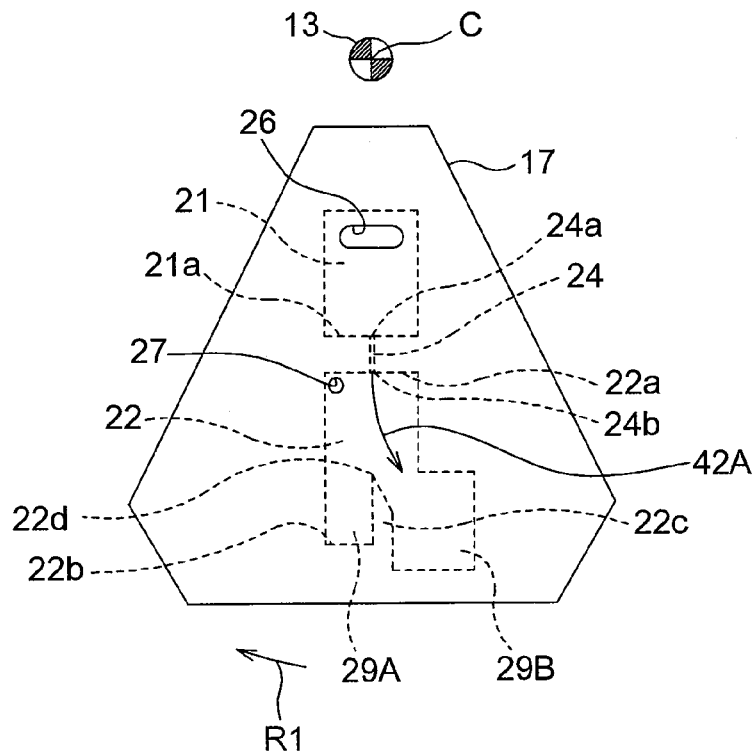
FIG. 6A is a plan view showing the direction of liquid delivery when the rotary platform is rotating clockwise in plan view.
Figure 6B:
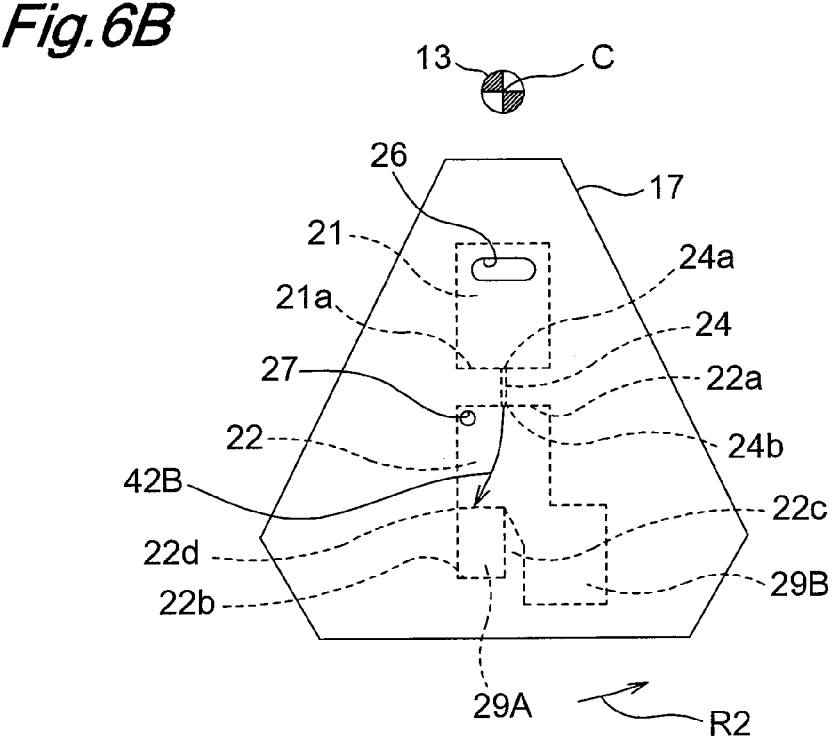
FIG. 6B is a plan view showing the direction of liquid delivery when the rotary platform is rotating counterclockwise in plan view.

Direction of the Coriolis force Fco acting on the infinitesimal element 41 is opposite to the rotation direction of the rotary platform 12 and is perpendicular to the relative movement of the infinitesimal element 41 to the rotary platform 12 (chamber chip 17). Specifically, when the rotary platform 12 rotates clockwise R1, the Coriolis force Fco acts on the infinitesimal element 41 in the counterclockwise direction R2 (toward right in FIG. 5). Therefore, when the rotary platform 12 rotates in the clockwise direction R1, flow path of the liquid 23 having entered through the outlet end section 24b into the branching chamber 22 is curved toward the counterclockwise direction R2 as schematically indicated by an arrow 42A. As a result, the liquid 23 flows into the branching compartment 29B positioned on the downstream side of the separation wall 23 in the counterclockwise direction R2, but does not flow into the branching compartment 29A positioned on the downstream side of the separation wall 23 in the clockwise direction R1 (FIG. 6A). When the rotary platform 12 rotates counterclockwise R2, the Coriolis force Fco acts on the infinitesimal element 41 in the clockwise direction R1 (toward left in FIG. 5). Therefore, when the rotary platform 12 rotates in the counterclockwise direction R2, flow path of the liquid 23 having entered through the outlet end section 24b into the branching chamber 22 is curved toward the clockwise direction R1 as schematically indicated by arrow 42B. As a result, the liquid 23 flows into the branching compartment 29A positioned on the downstream side of the separation wall 23 in the clockwise direction R1, but does not flow into the branching compartment 29B positioned on the downstream side of the separation wall 23 in the counterclockwise direction R2.

As is clear from the equation (3), the higher the rotation speed of the rotary platform 12 is, the larger the Coriolis force Fco becomes, and the lower the rotation speed of the rotary platform 12 is, the smaller the Coriolis force Fco becomes. This means that the amount of shift δ of the flow path of the liquid 23 becomes smaller at the position corresponding to the distal end d of the separation wall 22c in a low rotation speed range of the rotary platform 12, thus making it difficult to deliver the liquid 23 selectively into the branching compartments 29A and 29B. In this embodiment, the spread angle θe of the wall surface 22a from the outlet end section 24b of the guiding fluid passage 24 in the direction of arrangement of the branching chambers 29A and 29b is set to the obtuse angle (180 degrees) as previously described. This enables the liquid 23 to be selectively distributed into the branching compartments 29A and 29B by the Coriolis force Fco even when the rotation speed of the rotary platform 12 is relatively low (about between 600 rpm and 2,000 rpm). Specifically, the liquid 23 can be selectively distributed into the branching compartments 29A and 29B when the rotation speed of the rotary platform is in a range between 600 rpm and 3,300 rpm, particularly between 600 rpm and 2,000 rpm. This is supposedly because the influence of the Coanda effect is reduced by setting the spread angle θe to the obtuse angle. Specifically, it is supposed that the occurrence of vortices on the wall surface 22a around the outlet end section 24b is suppressed by due to that the extending angle θe is the obtuse angle, so that the liquid 23 is suppressed from being stagnating on or attached to the wall surface 22a around the outlet end section 24b due to the pressure drop caused by the attachment vortices.

In this embodiment, since the selective distribution of the liquid is achieved by the Coriolis force Fco, it is not necessary to provide the rotary platform 12 with a complicated structure such as overflow capillary which is required in the case of quantitation by the capillary effect. This makes the structure of the rotary platform 12 simpler and makes it possible to decrease the area required for providing the fluid passages and the chambers in the rotary platform 12. Further, it also increases the degree of freedom in designing the structure such as layout of chambers or the fluid passages and volumes of the branching compartments.

Figure 7:
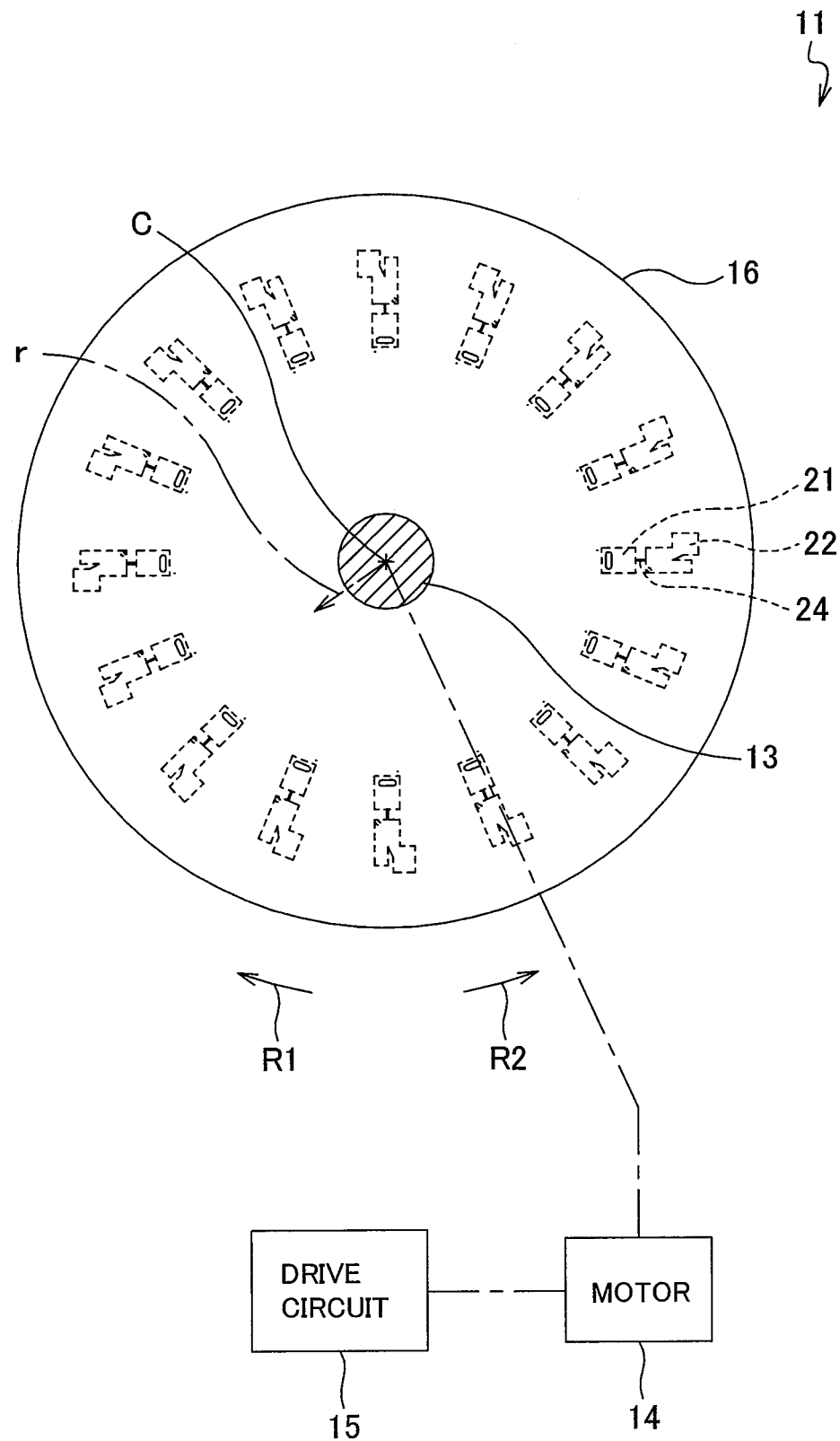
FIG. 7 is a schematic plan view showing an alternative structure of the rotary platform.

FIG. 7 shows an alternative structure of the rotary platform 12. In this alternative, the pre-branching chamber 21, the branching chambers 22, and the guiding fluid passage 24 are formed directly in the rotary platform body 16.

Second Embodiment

Figure 8:
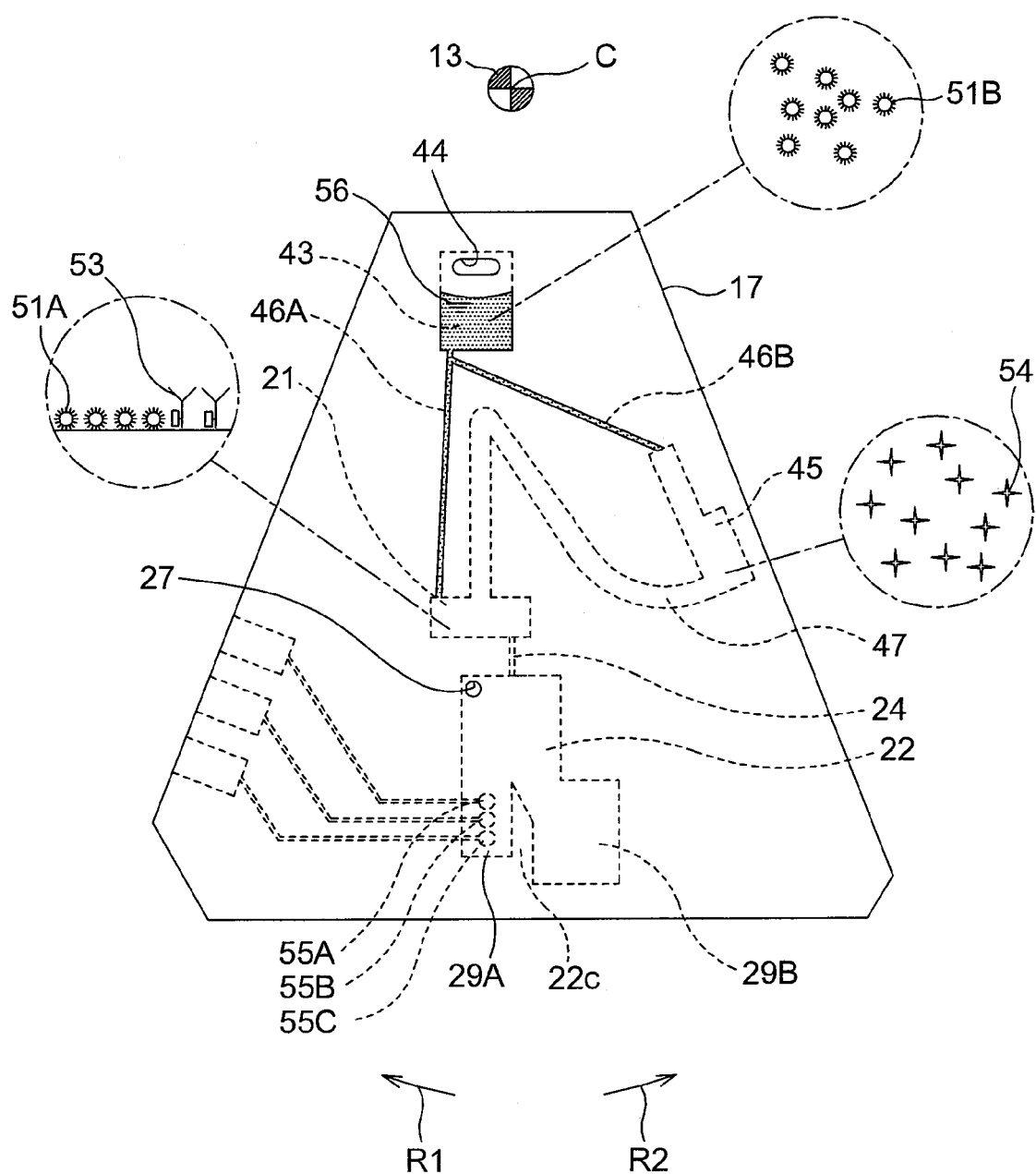
FIG. 8 is a schematic plan view of a chamber chip according to second embodiment of the present invention (when a blood sample is supplied)

A Second embodiment shown in FIG. 8 is an example where the chamber chip 17 is constituted as a bio-sensor used for electrochemical measurement of the concentration of CRP (C-reactive protein) whish is a kind of antigen in a blood serum.

The chamber chip 17 has an injection chamber 43 formed at a position nearer to the center of rotation C than the pre-branching chamber 21 in plan view. The injection chamber 43 is formed inside of the chamber chip 17 and is spatially closed. Formed in the chamber chip 17 is an injection port 44 that penetrates from a top wall of the injection chamber 43 to the top surface of the chamber chip 17 so that the inside of the injection chamber 43 fluidly communicates with the outside of the chamber chip 17. Unlike the first embodiment, the injection port 26 (refer to, for example, FIG. 2) is not formed in the pre-branching chamber 21.

An intermediate chamber 45 is also formed in the chamber chip 17 between the injection chamber 43 and the pre-branching chamber 21. The injection chamber 43 is fluidly connected to the pre-branching chamber 21 and the intermediate chamber 45 through fluid passages 46A and 46B formed in the chamber chip 17. The intermediate chamber 45 is fluidly connected to the pre-branching chamber 21 via a fluid passage 47.

The injection chamber 43 supports a reagent. The pre-branching chamber 21 supports a CRP (hereinafter referred to as sticking CRP 51A) and ALP (alkaline phosphatase) labeled antibody 53. Further, the intermediate chamber 45 supports an oxidation-reduction agent 54 for electrochemical detection. Furthermore, measurement electrodes 55A, 55B, and 55C are disposed in the branching compartment 29A of the branching camber 22 has measurement electrodes 55A, 55B, 55C.

Now a procedure for measuring the CRP concentration will be described. Initially, a blood serum 56 that includes CRP 51B to be measured is injected through the injection port 44 into the injection chamber 43. Although flowing into the fluid passage 46A and 46B, the blood serum 56 does not flow into the pre-branching chamber 21 and the intermediate chamber 45 because it held by the but is held by the capillary force at the outlet end section of the fluid passages 46A and 46B (FIG. 8).

Figure 9:
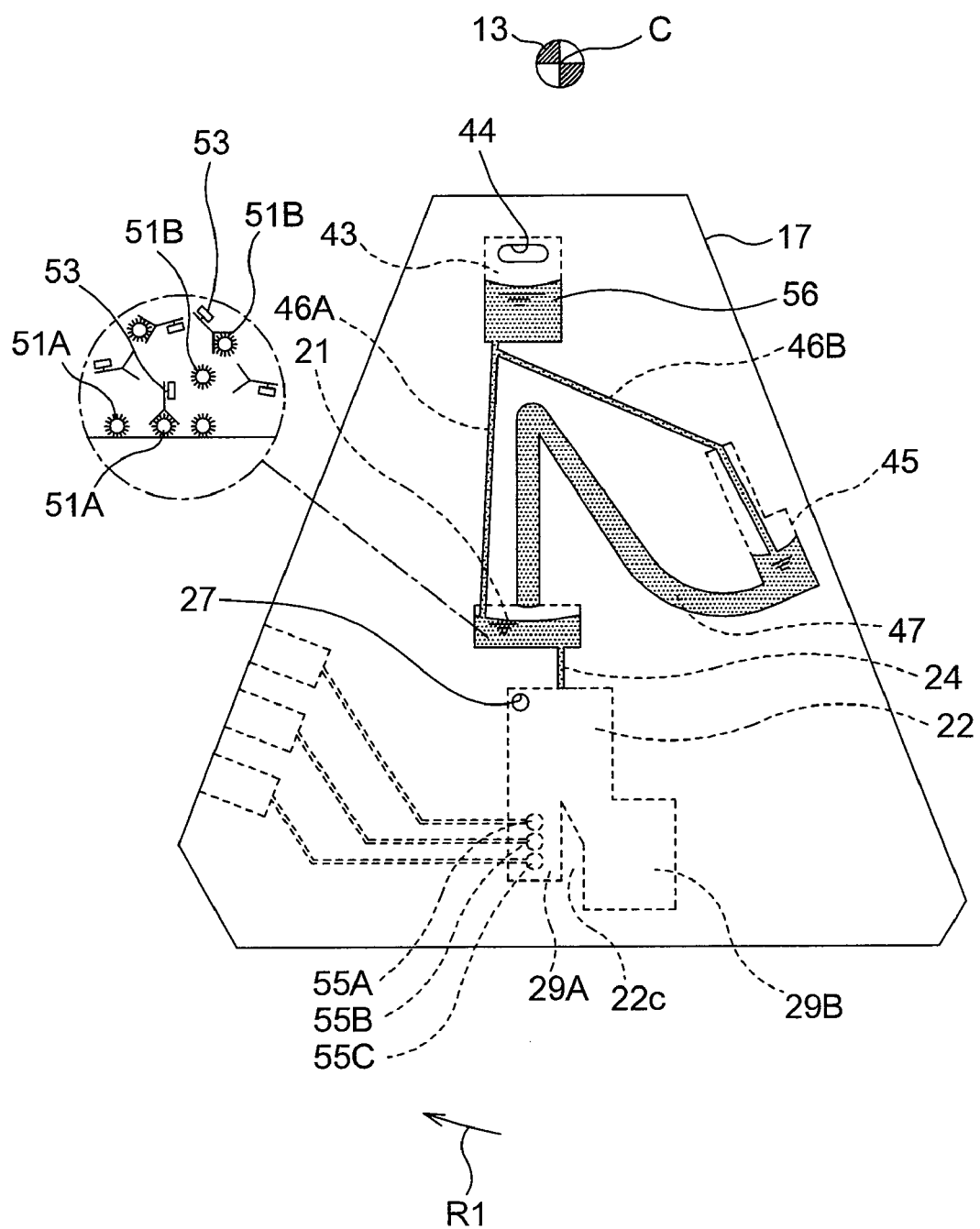
FIG. 9 is a schematic plan view of the chamber chip according to the second embodiment of the present invention (competitive reaction)

Then, the rotary platform 12 is driven to rotate clockwise R1 at a rotation speed RV1 (for example, 900 rpm). The centrifugal force generated by this rotation causes the blood serum 56 contained in the injection chamber 43 to flow through the fluid passages 46A and 46B into both of the pre-branching chamber 21 and the intermediate chamber 45 (FIG. 9). The blood serum 56 in the pre-branching chamber 21 is held by the capillary force at the outlet end section 24b of the guiding fluid passage 24. The blood serum 56 in the intermediate chamber 45 is held by the capillary force at an outlet end section of the fluid passage 47. Competitive reactions occur in the pre-branching chamber 21. Specifically, the ALP labeled antibody 53 competitively bonds with the CRP 51B of the blood serum 56 and the sticking CRP 51A. The proportion of the ALP labeled antibody 53 that bonds with the sticking CRP 51A depends on the concentration of the CRP 51B of the blood serum 56. The ALP labeled antibody 53 bonds with the CRP 51B in the blood serum, bonds with the sticking CRP 51A, or does not bond with either of the CRP 51A, 51B.

Figure 10:
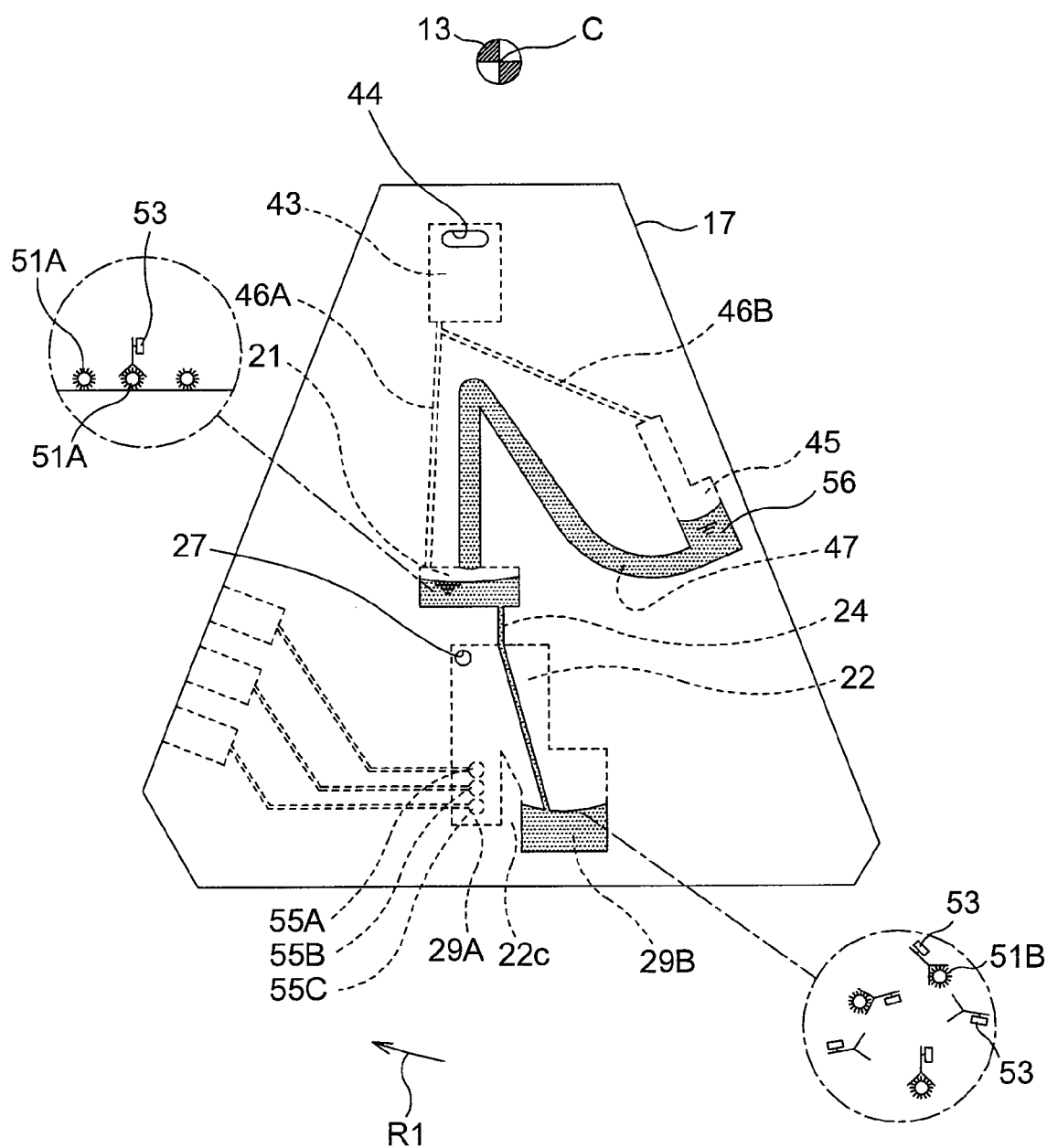
FIG. 10 is a schematic plan view of the chamber chip according to the second embodiment of the present invention (separation)
Figure 11:
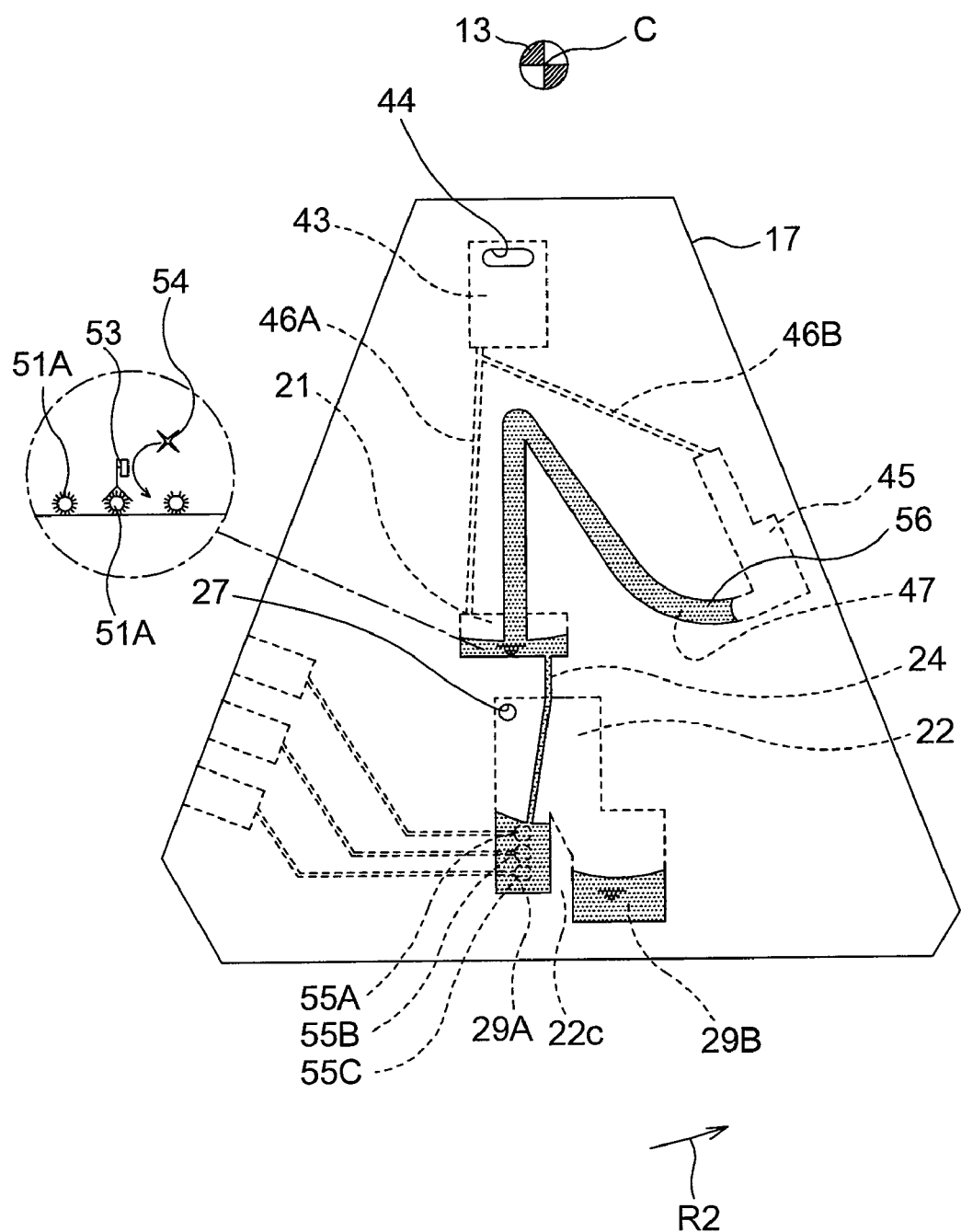
FIG. 11 is a schematic plan view of the chamber chip according to the second embodiment of the present invention (reaction with enzyme and measurement)

After the competitive reaction, the rotation speed is increased to a rotation speed RV2 (for example, 1500 rpm) higher than the rotation speed RV1 while keeping the rotation direction of the rotary platform 12 clockwise R1. As a result, the capillary force at the outlet end section 24b of the guiding fluid passage 24 exceeds the centrifugal force so that the blood serum 56 in the pre-branching chamber 21 flows through the outlet end section 24b into the branching chamber 22 (FIG. 10). When this occurs, the blood serum 56 in the intermediate chamber 45 is still held by the capillary force at the outlet end section of the fluid passage 47. Since the rotary platform rotates clockwise R1, the blood serum flowing through the outlet end section 24b into the branching chamber 22 is subjected to the Coriolis force acting counterclockwise R2, thereby casing that the flow path of the blood serum 56 flowing into the branching chamber 22 is deflected toward the counterclockwise direction R2. As a result, all of the blood serum 56 flowing through the outlet end section 24b into the branching chamber 22 flows into the branching compartment 29B positioned at a downstream side of the separation wall 22c in the counterclockwise direction R2. The blood serum 56 flowing into the branching compartment 29B includes the ALP labeled antibody 53 bonded with the CRP 51B in the blood serum and the ALP labeled antibody 53 not bonded with the CRP 51. On the other hand, the sticking CRP 51A and the ALP labeled antibody 53 remain in the pre-branching chamber 21. The delivery of the blood serum at the rotation speed RV2 has an effect of separating the ALP labeled antibody 53 bonded with the sticking CRP 51A and the ALP labeled antibody 53 not bonded with the sticking CRP 51A. The branching compartment 29B serves as a disposal chamber for the blood serum that is not necessary for measurement since the blood serum 56 that includes the ALP labeled antibody 53 not necessary for measurement flows into the branching compartment 29B.

Then, the rotation direction of the rotary platform 12 is reversed to counterclockwise R2 and the rotation speed is increased to a rotation speed RV3 (for example, 1,900 rpm) higher than the rotation speed RV2. As a result, the centrifugal force exceeds the capillary force at the outlet end section of the fluid passage 47. This causes that that the blood serum 56 in the intermediate chamber 45 that includes the oxidation-reduction agent 54 for electrochemical detection flows through the fluid passage 47 into the pre-branching chamber 21 and further flows through the guiding fluid passage 24 and the outlet end section 24b into the branching chamber 22. Since the rotary platform rotates counterclockwise R2, the blood serum 56 that flows through the outlet end section 24b into the branching chamber 22 receives Coriolis force acting clockwise R1 so that the flow path of the blood serum 56 flowing into the branching chamber 22 is curved toward the clockwise direction R1. As a result, all of the blood serum 56 flowing through the outlet end section 24b into the branching chamber 22 flows into the branching compartment 29A positioned at a downstream position of the separation wall 22c in the clockwise direction R1. In the pre-branching chamber 21, the oxidation and reduction reactions occur between the ALP labeled antibody 53 that bonds with the sticking CRP 51A and the oxidation-reduction agent 54 for electrochemical detection. This makes it possible to measure the quantity of the ALP labeled antibody 53 that bonds with the sticking CRP 51A (which depends on the concentration of CRP 51B in the blood serum 56 as previously described) by the electrochemical reaction between the blood serum 56 that has entered the branching compartment 29A and the electrodes 55A through 55C. The branching compartment 29A serves as a measuring chamber since the electrodes 55A through 55C are disposed therein and only the blood serum 56 necessary for measurement is supplied.

The order of the inflow of the blood serum 56 from the injection chamber 43 through the fluid passage 46A into the pre-branching chamber 21 and the inflow of the blood serum 56 from the intermediate chamber 45 through the fluid passage 47 into the pre-branching chamber 21 can be controlled by adjusting the strength of the centrifugal force which can be changed by setting of the depth and width of the chambers 43 and 21. The configuration of the fluid passage 47 having a bent flow path functions for delaying the delivery of the liquid from the intermediate chamber 45 into the pre-branching chamber 21 relative to the delivery of the liquid from the injection chamber 43 into the pre-branching chamber 21.

Other arrangements and operations of the second embodiment are similar to those of the first embodiment, therefore same elements is denoted by same reference numerals and description thereof will be omitted.

EXAMPLES

The chamber chip 17 according to the first embodiment of the present invention shown in FIGS. 1 to 3 was actually fabricated to be subjected to an experiment of selective distribution of small volume of liquid.

First, fabrication of the chamber chip 17 will be described. A die was made from steel with such protrusions formed in a cavity thereof by cutting operations that corresponded to the pre-branching chamber 21, the branching chamber 22, the guiding fluid passage 24, the injection port 26, and the air aperture 27. This die was used in injection molding of urethane resin to make the upper substrate 36. The guiding fluid passage 24 was formed with a width of 200 μm and a depth of 35 μm. The branching compartments 29A and 29B of the branching chamber 22 were formed both with a depth of 1 mm. The distance t between the distal end 22d of the separation wall 22c and the wall surface 22a was set to 4 mm. The lower substrate 37 formed from PET (polyethylene terephthalate) was bonded to the under surface of the upper substrate 36 made of urethane resin.

Figure 12:
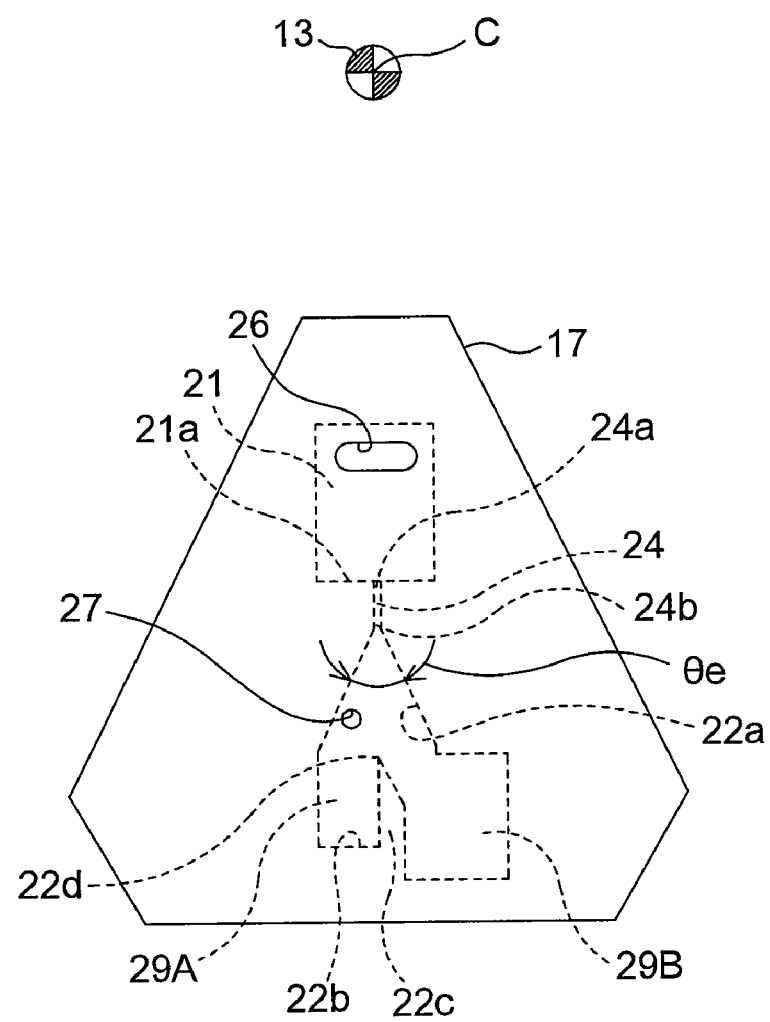
FIG. 12 is a schematic plan view of a comparative example of the chamber chip.

For the purpose of comparison, a chamber chip was made in the same structure as the chamber chip 17 of the first embodiment by the same manufacturing method except for that the spread angle θe of the wall surface 22a from the outlet end section 24 of the guiding fluid passage 24 in the direction of arrangement of the branching compartments 29A and 29B was set to an acute angle (45 degrees) as shown in FIG. 12. In the following descriptions, a reference numeral 17A will be used when referring to the chamber chip of the first embodiment whereas reference numeral 17B will be used when referring to the chamber chip of the comparative example.

First, 5 micro liters of the liquid 23 (prepared by mixing predetermined quantities of sample solution and reagent) was introduced into the pre-branching chamber 21 of the chamber chips 17A and 17B. Then, the chamber chips 17A and 17B were driven to rotate clockwise R1 around the center of rotation C at a speed of 800 rpm. This resulted in that the liquid 23 remained in the pre-branching chamber 21 without flowing into the branching chamber 22 in either of the chamber chips 17A, 17B.

When the rotation speed was subsequently increased while maintaining the rotation direction clockwise R1, flow of the liquid 23 from the pre-branching chamber 21 through the guiding fluid passage 24 into the branching chamber 22 occurred when the rotation speed exceeded 1,216 rpm in both of the chamber chips 17A and 17B. As shown in Table 1, in the inventive chamber chip 17A, the liquid 23 flowed only into the branching compartment 29B positioned on the downstream side of the separation wall 22c in the counterclockwise direction R2. In the chamber chip 17B (Comparative Example), on the other hand, substantially equal quantities of the liquid 23 flowed into the two branching compartments 29A and 29B separated from each other by the separation wall 22c.

After the rotation of the chamber chips 17A and 17B stopped, 5 micro liters of the liquid 23 was introduced again into the pre-branching chambers 21 of the chamber chips 17A and 17B. Then, the chamber chips 17A and 17B were driven to rotate counterclockwise R2 and the rotation speed was gradually increased. When the rotation speed exceeded 1146 rpm, flow of the liquid 23 from the pre-branching chamber 21 through the guiding fluid passage 24 into the branching chamber 22 occurred in both the chamber chips 17A and 17B. As shown in Table 1, in the chamber chip 17A, the liquid 23 flowed only into the branching compartment 29A positioned on the downstream side of the separation wall 22c in the clockwise direction R1. In the chamber chip 17B (comparative example), on the other hand, substantially equal quantities of the liquid 23 flowed into the two branching compartments 29A and 29B.

TABLE 1

| | Quantity of liquid flowing into branching compartments 29A and 29B (μL) | | | |
|---|---|---|---|---|
| | Chamber chip 17A (present invention) | | Chamber chip 17B (comparative example) | |
| | Branching compartment 29A (Left) | Branching compartment 29B (Right) | Branching compartment 29A (Left) | Branching compartment 29B (Right) |
| Clockwise R1 | 0 | 4.9 | 1.5 | 2.4 |
| Counter-clockwise R2 | 5.0 | 0 | 2.2 | 1.7 |

Figure 13:
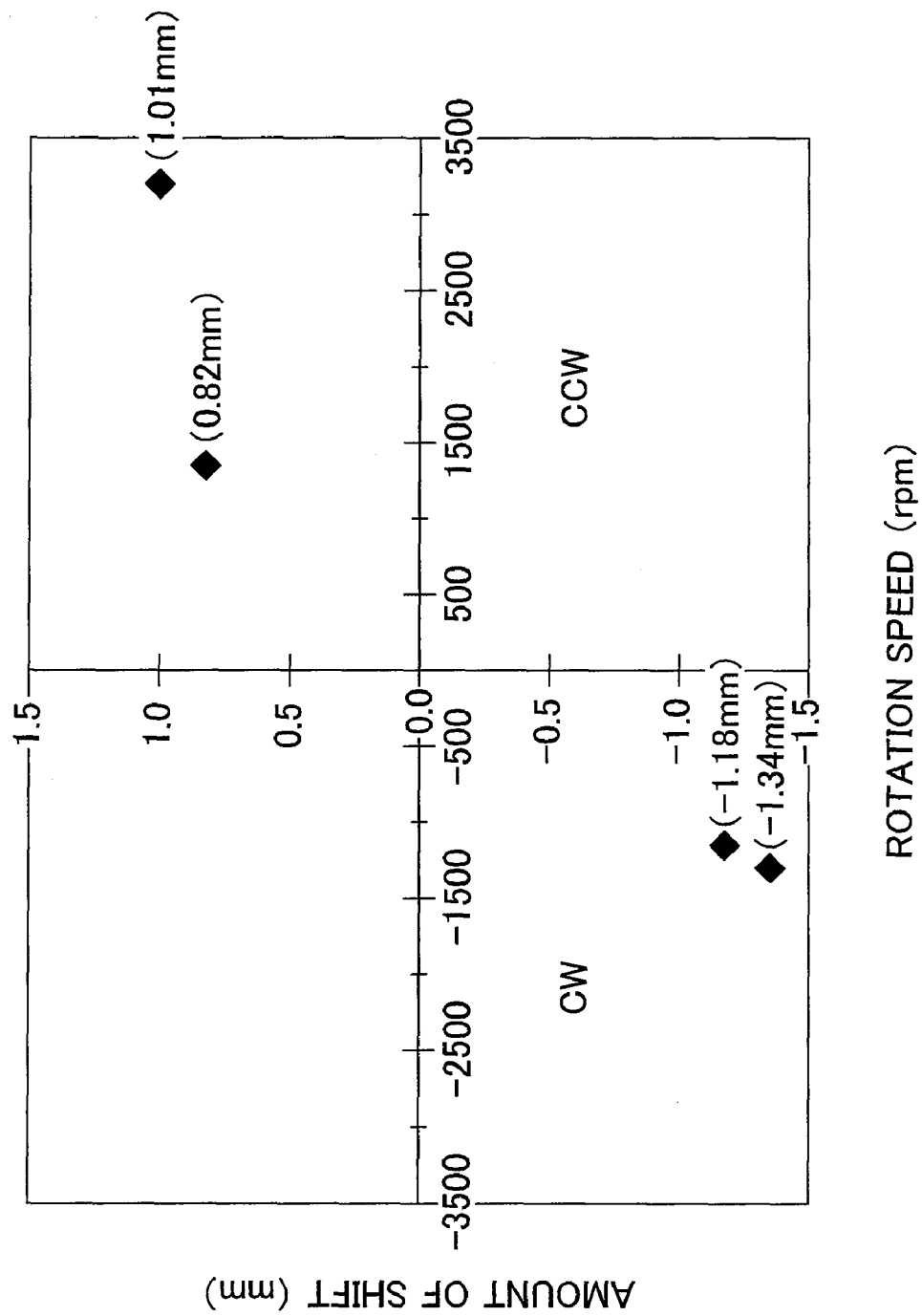
FIG. 13 is a graph showing the relation between a rotation speed and an amount of shift of liquid in the example of the present invention.
Figure 14:
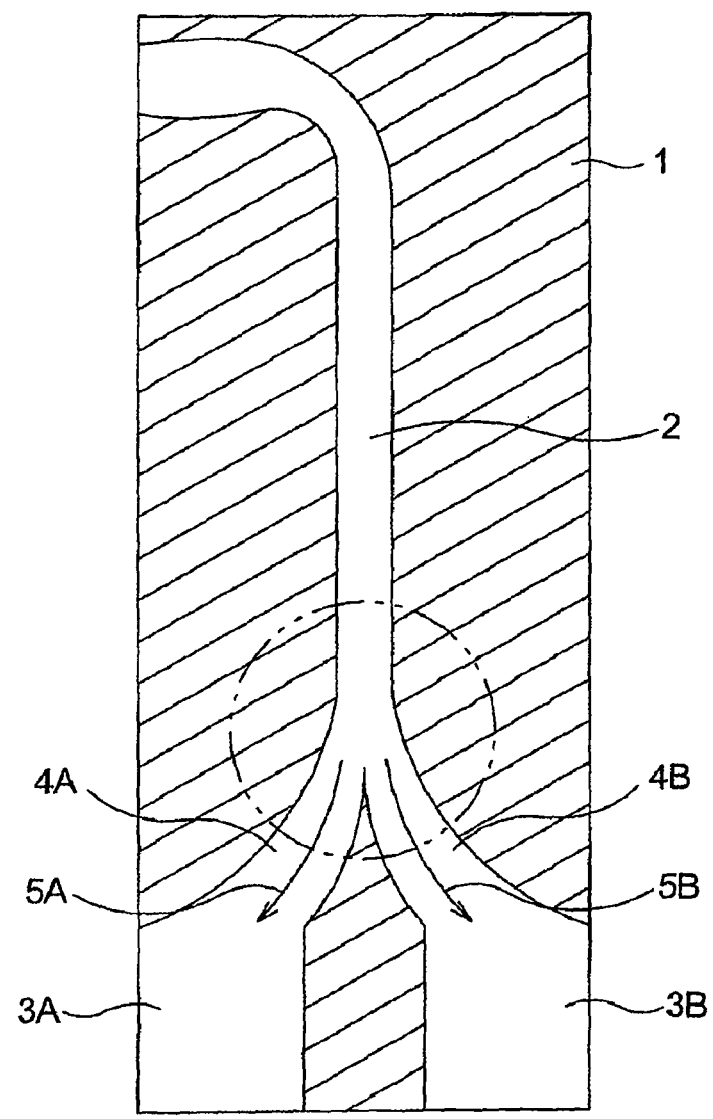
FIG. 14 is a partial plan view of a rotary platform of the prior art having a branching fluid passage of inverted Y-like shape.
Figure 14:

The amount of the shift δ that occurred in the chamber chip 17A was measured. The distance t was 4 mm as previously described. The results of measurements are shown in FIG. 13. It can be seen that, when the rotation speed is about 1,500 rpm or higher, shift δ of about 0.8 mm or more can be obtained regardless of the direction of rotation. An amount of shift δ of about 0.8 mm or more is sufficient to deliver the liquid 23 selectively to either of the branching compartments 29A, 29B.

As described above, the chamber chip 17B of the comparative example having a small extending angle θe of the wall surface 22a is not capable of controlling the distribution of the liquid into the branching compartments 29A and 29B by the direction of rotation. Contrarily to this, the chamber chip 17A of the present invention is capable of selectively distributing the liquid into the two branching compartments 29A and 29B of the branching chamber 22 by setting the direction of rotation to either clockwise R1 or counterclockwise R2. This is supposedly because the influence of the Coanda effect was reduced by setting the extending angle θe of the wall surface 22a to the obtuse angle as previously described.

The present invention is not limited to the embodiments described above and various modifications can be conceived. For example, the pre-branching chamber may be either a chamber into which the liquid is directly poured, or a chamber into which the liquid flows through a fluid passage from another chamber positioned upstream. Also any of the plurality of chambers or all thereof may be connected to the chamber positioned downstream via a fluid passage.

What is claimed is:

1. A liquid delivery apparatus comprising:
a rotary platform capable of rotating about a center of rotation;
a pre-branching chamber provided in the rotary platform and accommodating a liquid;
a guiding fluid passage provided in the rotary platform, having an inlet end section that is connected to the pre-branching chamber and holds the liquid in the pre-branching chamber by a capillary force, extending from the inlet end section in a direction away from the center of rotation, and having an outlet end section at an opposite side to the inlet end section;
a branching chamber provided in the rotary platform at a position farther from the center of rotation than the pre-branching chamber, spatially enclosed except for an air aperture, and having a first wall surface that is arranged at a centripetal direction side and at which the outlet end section of the guiding fluid passage opens, second wall surface that is arranged at a centrifugal direction side and is opposed to the first wall surface, and separation wall that extends from the second wall surface toward the first wall surface to define a plurality of branching compartments, wherein the first wall surface has a spread angle from the outlet end section of the guiding fluid passage that is an obtuse angle at least in a direction of arrangement of the plurality of branching compartments, and the separation wall has a distal end that is arranged in the vicinity of a imaginary line extending in the centrifugal direction from the outlet end section of the guiding fluid passage and opposed to the first wall surface with a distance; and
a rotation drive unit for rotating the rotary platform about the center of rotation at a rotation speed between 1500 rpm and 2000 rpm,
wherein the liquid is a blood serum, and
wherein a cross sectional area of the guiding fluid passage is in a range between 1 μm² and 4 mm².

2. The liquid delivery apparatus according to claim 1, wherein the spread angle of the first wall surface is between 120 degrees and 300 degrees.

3. The liquid delivery apparatus according to claim 1, wherein the rotation drive unit rotates the rotary platform at a rotation speed where the centrifugal force exceeding the capillary force is exerted on the liquid held at the inlet end section of the guiding fluid passage, thereby causing the liquid in the branching chamber to flow through the guiding fluid passage into the branching compartment positioned opposite to a rotation direction of the rotary platform with respect to the separation wall.

4. A liquid delivery method comprising:
preparing a rotary platform comprising:
a pre-branching chamber;
a guiding fluid passage having an inlet end section that is connected to the pre-branching chamber and an outlet end section at an opposite side to the inlet end section and having a cross sectional area in a range between 1 µm² and 4 mm²; and
a branching chamber provided at a position farther from the center of rotation than the pre-branching chamber, spatially enclosed except for an air aperture, and having a first wall surface that is arranged at a centripetal direction side and at which the outlet end section of the guiding fluid passage opens, second wall surface that is arranged at a centrifugal direction side and is opposed to the first wall surface, and separation wall that extends from the second wall surface toward the first wall surface to define a plurality of branching compartments, the first wall surface having a spread angle from the outlet end section of the guiding fluid passage that is an obtuse angle at least in a direction of arrangement of the plurality of branching compartments, the separation wall having a distal end that is arranged in the vicinity of a imaginary line extending in the centrifugal direction from the outlet end section of the guiding fluid passage and is opposed to the first wall surface with a distance;
supplying a blood serum to the pre-branching chamber so that the blood serum is held in the pre-branching chamber by a capillary force at the inlet end section of the guiding fluid passage;
rotating the rotary platform about the center of rotation at a rotation speed between 1500 rpm and 2000 rpm so that a centrifugal force exceeding the capillary force is exerted on the blood serum, thereby causing the blood serum in the pre-branching chamber to flow through the guiding fluid passage into the branching compartment positioned opposite to a rotation direction of the rotary platform with respect to the separation wall.

5. The liquid delivery method according to claim 4, wherein the spread angle of the first wall surface is between 120 degrees and 300 degrees.

* * * * *